United States Patent
Winter et al.

(10) Patent No.: US 12,023,083 B2
(45) Date of Patent: Jul. 2, 2024

(54) ELECTROSURGICAL SYSTEM FOR GENERATING HIGH-FREQUENCY ALTERNATING CURRENT

(71) Applicant: OLYMPUS WINTER & IBE GMBH, Hamburg (DE)

(72) Inventors: Hanno Winter, Berlin (DE); Tino Kirfe, Berlin (DE); Frank Breitsprecher, Berlin (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 704 days.

(21) Appl. No.: 16/060,993

(22) PCT Filed: Dec. 30, 2016

(86) PCT No.: PCT/EP2016/082938
§ 371 (c)(1),
(2) Date: Jun. 11, 2018

(87) PCT Pub. No.: WO2017/114957
PCT Pub. Date: Jul. 6, 2017

(65) Prior Publication Data
US 2018/0360522 A1 Dec. 20, 2018

(30) Foreign Application Priority Data
Dec. 30, 2015 (DE) .......................... 102015226846.2

(51) Int. Cl.
*A61B 18/12* (2006.01)
*A61B 18/14* (2006.01)
*A61B 18/00* (2006.01)

(52) U.S. Cl.
CPC ...... *A61B 18/1206* (2013.01); *A61B 18/1492* (2013.01); *A61B 2018/00678* (2013.01);
(Continued)

(58) Field of Classification Search
CPC ............ A61B 18/1206; A61B 18/1492; A61B 2018/00678; A61B 2018/00702; A61B 2018/00875; A61B 2018/00672
(Continued)

(56) References Cited

U.S. PATENT DOCUMENTS 6,409,722 B1 * 6/2002 Hoey ..................... A61B 18/18
606/41
9,820,664 B2 * 11/2017 Hoitink ................ A61B 5/6859
(Continued)

FOREIGN PATENT DOCUMENTS

CN 101106950 A 1/2008
CN 103118614 A 5/2013
(Continued)

OTHER PUBLICATIONS

May 28, 2020 Office Action issued in Japanese Patent Application No. 2018-534687.
(Continued)

*Primary Examiner* — Linda C Dvorak
*Assistant Examiner* — Lindsay Regan Lancaster
(74) *Attorney, Agent, or Firm* — Oliff PLC

(57) ABSTRACT

An electrosurgical system for generating high-frequency alternating current for an ablation of body tissue, containing a high-frequency voltage supply unit which is or is to be electrically connected to a first and second electrode, and which is configured to supply the electrodes with a high-frequency alternating voltage. The electrosurgical system further includes a feedback unit which is electrically connected to the first and second electrodes and which is configured to generate and transmit an output signal dependent on the electrical resistance between the first and second electrodes. The electrosurgical system also includes a control unit that is configured to control the high-frequency
(Continued)

voltage supply unit in such a way as to be able to automatically switch between at least one first and one second operating mode.

11 Claims, 4 Drawing Sheets

(52) U.S. Cl.
CPC ............. *A61B 2018/00702* (2013.01); *A61B 2018/00875* (2013.01)

(58) Field of Classification Search
USPC ........................................................... 606/34
See application file for complete search history.

(56) References Cited

U.S. PATENT DOCUMENTS

| | | | | |
|---|---|---|---|---|
| 2002/0032439 | A1* | 3/2002 | Hareyama | A61B 18/1206 606/38 |
| 2002/0151884 | A1* | 10/2002 | Hoey | A61B 18/14 606/34 |
| 2003/0212395 | A1* | 11/2003 | Woloszko | A61B 18/149 606/41 |
| 2003/0233088 | A1* | 12/2003 | Ohyama | A61B 18/149 606/46 |
| 2006/0217707 | A1* | 9/2006 | Daniel | A61B 18/1477 606/50 |
| 2009/0149848 | A1* | 6/2009 | Werneth | A61B 18/18 606/33 |
| 2009/0234351 | A1 | 9/2009 | Desinger et al. | |
| 2010/0030212 | A1* | 2/2010 | Aramayo | A61B 18/1402 606/41 |
| 2010/0076430 | A1* | 3/2010 | Romero | A61B 18/1445 606/51 |
| 2010/0191238 | A1* | 7/2010 | Kornerup | A61B 18/14 606/47 |
| 2011/0160725 | A1* | 6/2011 | Kabaya | A61B 18/1206 606/42 |
| 2012/0101538 | A1* | 4/2012 | Ballakur | A61B 18/10 607/3 |
| 2013/0338665 | A1 | 12/2013 | Tanaka et al. | |
| 2014/0093227 | A1* | 4/2014 | McGuffey | H05B 3/16 392/465 |
| 2014/0276768 | A1 | 9/2014 | Juergens et al. | |
| 2014/0350401 | A1* | 11/2014 | Sinelnikov | A61B 17/2202 600/439 |
| 2015/0032099 | A1* | 1/2015 | Larson | A61B 18/1233 606/35 |
| 2015/0272657 | A1* | 10/2015 | Yates | A61B 18/1206 606/34 |
| 2016/0066986 | A1* | 3/2016 | Winter | A61B 18/14 606/41 |
| 2016/0228023 | A1* | 8/2016 | Govari | A61B 18/1492 |
| 2017/0348064 | A1 | 12/2017 | Stewart et al. | |

FOREIGN PATENT DOCUMENTS

| | | |
|---|---|---|
| CN | 103997979 A | 8/2014 |
| CN | 104582606 A | 4/2015 |
| DE | 10 2004 041 681 A1 | 2/2006 |
| DE | 10 2012 220 658 A1 | 5/2014 |
| EP | 2 213 256 A1 | 8/2010 |
| EP | 2329782 B1 | 5/2014 |
| EP | 2767249 A2 | 8/2014 |
| EP | 2851025 A2 | 3/2015 |
| JP | H07-79996 A | 3/1995 |
| JP | 2000-157556 A | 6/2000 |
| JP | 2010-158525 A | 7/2010 |
| WO | 2008/102154 A2 | 8/2008 |
| WO | 2011/052349 A1 | 5/2011 |

OTHER PUBLICATIONS

Mar. 29, 2017 International Search Report issued in International Patent Application No. PCT/EP2016/082938.
Mar. 29, 2017 Written Opinion issued in International Patent Application No. PCT/EP2016/082938.
Aug. 11, 2016 German Office Action issued in German Patent Application No. DE 10 2015 226 846.2.
Jun. 29, 2020 Chinese Office Action issued in Chinese Patent Application No. 201680076548.1.

* cited by examiner

ELECTROSURGICAL SYSTEM FOR GENERATING HIGH-FREQUENCY ALTERNATING CURRENT

This application claims the benefit of PCT/EP2016/082938, filed Dec. 30, 2016, which in turn claims priority to DE 102015226846.2, filed Dec. 30, 2015. The disclosure of the prior applications is hereby incorporated by reference herein in its entirety.

FIELD OF INVENTION

The invention relates to an electrosurgical system for generating high-frequency current for an ablation of body tissue and a method of operating such an electrosurgical system.

BACKGROUND

High-frequency alternating current for the ablation of body tissue is used, inter alia, for an endovenous treatment of venous insufficiency. During such treatment, high-frequency energy is locally applied in a precisely dosed manner to venous tissue to be treated via an applicator, which has the effect that a respective vein contracts and closes. This is also referred to as thermal occlusion. Compared to conventional procedures, such as vein stripping, and also compared to other endovenous procedures, which use e.g. a laser, the high-frequency ablation is a particularly gentle method and is, in addition, easy and safe to perform. The pain caused as well as the risk of scarring, infections and haematomas are also very small. Another advantage of the high-frequency ablation is that it can be performed as an outpatient treatment and that patients treated are mobile shortly after receiving such treatment.

High-frequency ablation is also used for tumor treatment.

SUMMARY

The invention is based on the object of providing an improved electrosurgical system, in particular for being used in the ablation of body tissue.

Pursuant to the invention, an electrosurgical system for generating high-frequency alternating current for an ablation of body tissue is proposed in order to achieve this object, wherein said system comprises a high-frequency voltage supply unit which is or is to be electrically connected to a first and second electrode, and which is configured to supply said electrodes with a high-frequency alternating voltage. The electrosurgical system further comprises a feedback unit which is electrically connected to the first and second electrodes and which is configured to generate an output signal dependent on the electrical resistance between the first and second electrodes. For controlling the high-frequency supply unit, the electrosurgical system comprises a control unit that is configured to control the high-frequency voltage supply unit in such a way as to be able to automatically switch between at least one first and one second operating mode, wherein in the first operating mode the alternating voltage is limited by a first limit value $U_1$, and in the second operating mode the alternating voltage is limited by a second limit value $U_2$, wherein $U_1$ is greater than $U_2$. An automatic switching from the first operating mode into the second operating mode occurs if a rate of increase of the electrical resistance between the first and second electrodes exceeds a predetermined limit value G.

The invention includes the finding that, during the coagulation of tissue, the resistance of the tissue increases, starting from a low tissue resistance to high tissue resistance of dried out tissue. The respective tissue resistance detected by the electrosurgical system is indicated to the user by means of a discernible signal, e.g. an acoustic signal. The discernible signal changes along with the tissue resistance; the detected tissue resistance may e.g. be indicated by the frequency of the acoustic signal so that the pitch of the signal increases with the increase of the tissue resistance. During the vein ablation, the user or the treating physician, respectively, can vary the speed with which he guides the applicator along the vein depending on the audio signal he hears. One problem in this context is that shortly before the tissue dries out and the pertaining risk that the applicator might stick to it, the tissue resistance increases very fast and virtually abruptly, so that often the physician is not able to react quickly enough, i.e. is not able to move the applicator fast enough.

The electrosurgical system pursuant to the invention makes it possible to prevent a quasi-abrupt increase of the resistance tissue by reducing, as early as at the beginning of this abrupt increase, an output of the first and second electrodes through a reduction of the alternating current supplied to the electrodes. Therefore, the second limit value $U_2$ should preferably be chosen in such a way that the heat output will be clearly reduced through a switching from the first into the second operating mode.

Such an automatic reduction of the heat output gives the user of the electrosurgical system more time to react to the output signal and the electrical resistance of the body tissue between the two electrodes implied by it. A reaction in this context may typically be a change of a position of the first and second electrodes at the body tissue to be treated.

The advantage of the electrosurgical system pursuant to the invention is therefore that a drying out of the body tissue treated with the electrosurgical system and, thus, a sticking of the applicator to the tissue can be prevented. Thus, for example the drying of blood on the first or the second electrode can be prevented. Furthermore, the therapy duration required for the treatment can be shortened due to better control over the coagulation of the tissue, since interruptions of the therapy, for example for cleaning the two electrodes from dried out tissue, are avoided.

In addition, an electrosurgical system pursuant to the invention also allows for initially emitting a high heat output into the tissue which leads to a fast warming of the body tissue to be treated. Before the body tissue dries out, the control unit automatically reduces the voltage and, thus, also the heat output. Therefore, a very high heat output of the electrosurgical system can be used during a therapy phase in which a quick heating up of the body tissue is desired without incurring an increased risk of the tissue drying out. This also contributes to a short therapy duration. This makes the electrosurgical device pursuant to the invention particularly safe and easy to use. Especially a quick reaction of the user in order to prevent the tissue from drying out is no longer required.

The automatic switching between operating modes by the control unit does not mean that the additional option of manual switching is excluded. Instead, the control unit in one embodiment of the electrosurgical system is further configured to receive an input signal of a user and to perform a switching between the first and the second operating mode depending on the input signal.

In the following, preferred embodiments of the electrosurgical system pursuant to the invention are described.

In a particularly preferred embodiment, the control unit is further configured to control the high-frequency voltage supply unit in such a way that an automatic switching from the second into the first operating mode occurs when the electrical resistance between the first and second electrodes is below a predefined limit value. Thus, the electrosurgical system pursuant to this embodiment can automatically switch back to a high heat output after having automatically switched into an operating mode with low heat output, if the electrical resistance of the tissue surrounding the two electrodes is not too high. In this context, a predetermined limit value W is preferably chosen in such a way that a switching back will occur automatically if said tissue is not already dried out. Thus, the therapy duration is reduced, since the user of the electrosurgical system does not have to test the electrical resistance of the tissue manually first in order to adjust the alternating voltage present at the two electrodes and thus the heat output. Furthermore, it is advantageous to automatically limit the alternating voltage at the beginning of a treatment of the body tissue to the first limit value $U_1$ so that high heat output necessary at the beginning of a treatment is provided by the electrosurgical system pursuant to the invention.

Preferably, the electrosurgical system further comprises a processing unit which is electrically connected to the first and second electrodes and configured to receive an electrical response signal via the first and second electrodes, to determine the electrical resistance between the first and second electrodes or a value representing the electrical resistance based on said electrical response signal and to generate and output a control signal dependent on the electrical resistance, and wherein the feedback unit and the control unit are further configured to receive the control signal.

In a particularly preferred embodiment, the feedback unit has a loudspeaker and is configured to output the output signal via the loudspeaker as an audible sound. Such an output of the sound can be performed in such a way that a frequency of the audible sound is e.g. proportional to the electrical resistance between the first and second electrodes. In another example of this embodiment the sound is output via a series of individual sounds with respective interruptions of the sound. In this example, the duration of the respective interruption of the sound depends on the electrical resistance between the first and second electrodes. The feedback unit may also be configured in such a way that a combination of a frequency change and an interruption of the sound are output as the output signal. For example, for a too high rate of increase of the electrical resistance, not only the frequency of the audible sound may change, but individual sounds may be output, in particular as a beep sound. The output of the output signal as an audible sound has the advantage that a user of the electrosurgical system does not have to additionally look at an optical output, such as a monitor, in order to obtain information on the electrical resistance between the first and second electrodes in the form of the output signal.

In another alternative embodiment, the feedback unit comprises an optical output and is configured to output the output signal via the optical output as discernible visual information. Such visual information may for example consist in a change of a color of image points of the optical output or in a change of an operating state of a light emitting diode.

In a further embodiment, the feedback unit is configured to be connected to an external optical output or to an external loudspeaker in an electrically conductive manner. In this embodiment, a repair of the loudspeaker or of the optical output is facilitated, since the respective external component may be replaced without the need to replace or repair the electrosurgical system.

Preferably, the limit value $U_2$ is between 50% and 80%, preferably 70%, of the first limit value $U_1$. Such a relationship between the second limit value $U_2$ and the first limit value $U_1$ has turned out to be particularly advantageous for preventing body tissue to be treated from drying out. In case of 50% to 80% of the limit value $U_1$, the corresponding heat output of the two electrodes is reduced to such an extent that the rate of increase of the electrical resistance between the two electrodes is reduced in such a way that the user of the electrosurgical system has sufficient time for changing a position of the electrodes at the tissue as a reaction to the output signal and to thus prevent the respective body tissue from drying out.

In another embodiment, the amplitude of the alternating voltage $U_1$ and/or the amplitude of the alternating voltage $U_2$ can be entered manually by the user via a user interface and be received by the control unit as a user signal provided by the user interface.

Typical values for the limit value $U_1$ are in the range between 80V to 200V, for example 100V.

In a particularly preferred embodiment, the control unit is further configured to store the electrical resistance between the first electrode and second electrodes or a value representing the resistance for a predetermined period of time, to compare the electrical resistance or the representing value at a current point in time with the electrical resistance or the representing value at an earlier point in time and to thus determine the rate of increase of the electronical resistance. In this context, the determination of the rate of increase may also be performed via a plurality of electrical resistances detected at an earlier point in time or of values representing the resistance. An increase of the rate of increase of the electrical resistance may also be determined by determining the electrical resistance or the value representing the resistance at fixed time intervals and, if the difference to the value determined before the respective interval exceeds a predetermined limit value, a too high rate of increase of the predetermined value will be detected and a switching from the first into the second operating mode will be executed by the control unit.

In one embodiment, the control unit is further configured to automatically switch between a number of other operating modes with other limit values $U_3, \ldots, U_n$, with successively decreasing amplitudes, which are smaller than the amplitude of $U_2$, wherein an automatic switching from one of the operating modes with the limit value $U_i$ into the operating mode with the next smaller limit value $U_{i+1}$ for the respective alternating voltage occurs when the rate of increase of the electrical resistance between the first and second electrodes is above a predetermined limit value $G_i$, assigned to the operating mode with the limit value $U_i$. Through this, the heat output of the two electrodes can be further reduced in an advantageous manner. This may be reasonable, inter alia, if the electrical resistance of the tissue to be treated shows a high rate of increase even if the alternating voltage with the limit value $U_2$ which is reduced compared to the alternating voltage with the limit value $U_1$ is supplied. In this case, the heat output of the two electrodes should be further reduced in order to prevent the body tissue from drying out too much.

Preferably, the electrosurgical system pursuant to the invention comprises an applicator, where the first and the second electrodes form a bipolar electrode configuration in the applicator, wherein the first electrode is arranged at a preferably rounded tip of a distal end of the applicator and the second electrode is arranged at a distance of between 0.5 cm and 3 cm from the first electrode at the distal end of the applicator. In an alternative embodiment, the electrodes are arranged at two different distal ends of the applicator, wherein the two distal ends are neighboring ends. Preferably, the applicator is configured in such a way that it can be guided to the body tissue to be treated via a catheter. This facilitates a surgical treatment of the body tissue and, in doing so, reduces scarring and the regeneration period of a patient after such a treatment, since only a small amount of healthy body tissue of the patient must be harmed.

In addition, a method of operating an electrosurgical system comprising the following method steps is proposed in order to achieve the above mentioned object:

applying an alternating voltage to a first electrode and a second electrode of an applicator, generating and outputting an output signal dependent on an electrical resistance between the first and second electrodes, controlling the alternating voltage in such a way as to be able to automatically switch between at least one first and one second operating mode of the applicator, wherein in the first operating mode the alternating voltage is limited by a first limit value $U_1$, and in the second operating mode the same is limited by a second limit value $U_2$, wherein $U_1$ is greater than $U_2$, and wherein an automatic switching from the first operating mode into the second operating mode occurs if a rate of increase of the electrical resistance between the first and second electrodes exceeds a predetermined limit value G.

Preferably, the controlling of the alternating voltage is performed in such a way that an automatic switching from the second operating mode into the first operating mode occurs if the electrical resistance between the first and second electrode is below a predetermined limit value W.

In a preferred embodiment, the method comprises the following additional method steps:

determining the electrical resistance or a value representing the electrical resistance between the first and second electrodes, generating and outputting a control signal dependent on the electrical resistance, storing the electrical resistance or the value representing the electrical resistance for a predetermined period of time and determining the rate of increase of the electrical resistance by comparing the electrical resistance or the representing value at a current point in time with the electrical resistance or the representing value at an earlier point in time.

Another aspect of the invention relates to the use of an electrosurgical system of the above described type for the thermal necrosis of unwanted body tissue, in particular for the endovenous treatment of vein insufficiency.

Another aspect relates to the application of the above described method in the context of an ablation of unwanted tissue, in particular in the context of an endovenous treatment of vein insufficiency.

BRIEF DESCRIPTION OF THE DRAWINGS

In the following, the invention is to be described in more detail based on exemplary embodiments with reference to the figures. The figures show the following.

DETAILED DESCRIPTION

Figure 1:
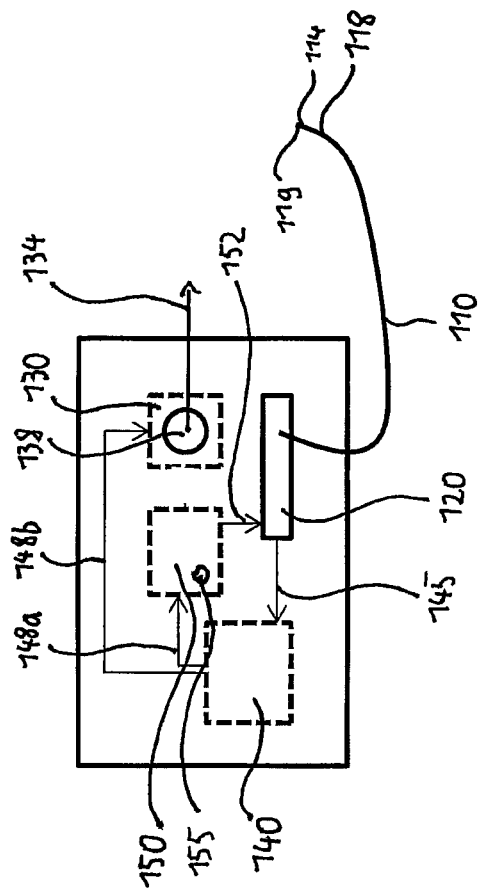
FIG. 1 an electrosurgical system for generating high-frequency alternating current with an applicator pursuant to an exemplary embodiment pursuant to the invention.

FIG. 1 shows an electrosurgical system 100 for generating high-frequency alternating voltage comprising an applicator 110 pursuant to an exemplary embodiment pursuant to the invention.

The electrosurgical system 100 comprises the applicator 110, a high-frequency voltage supply unit 120, a feedback unit 130, a processing unit 140 and a control unit 150.

The high-frequency voltage supply unit 120 is electrically connected to a first and second electrode 114, 118 and configured to supply these electrodes 114, 118 with an alternating voltage. The two electrodes 114, 118 form a bipolar electrode configuration at the applicator 110 and are arranged at a distal end 119 of the applicator. The first electrode 114 is arranged at an rounded tip of the distal end 119 and the second electrode is arranged at a distance of between 0.5 cm and 3 cm from the first electrode 114.

The feedback unit 130 is electrically connected to the first and second electrodes 114, 118 and configured to generate and output, depending on an electrical resistance between the first and second electrodes 114, 118, an output signal 134 which is discernible for a user. To this end, the feedback unit comprises a sound generator and a loudspeaker 138 so that the output signal 134 can be output via the loudspeaker 138 as a sound that is audible to a user of the electrosurgical system 100. In the illustrated exemplary embodiment, the sound generator is shown in such a way that the frequency of the generated sound is proportional to the electrical resistance between the first electrode 114 and the second electrode 118. Therefore, for a treatment of the body tissue, the pitch of the audible sound will increase with the increase of the electrical resistance of the tissue due to the drying out caused by a heat output of the two electrodes 114, 118. Therefore, the user can infer the drying out of the body tissue treated by means of the two electrodes 114, 118 from the pitch of the output signal 134.

The processing unit 140 is electrically connected to the first and second electrodes 114, 118. It is configured to receive an electrical signal 145 via the first and second electrodes 114, 118, to determine the electrical resistance between the first and second electrodes 114, 118 or a value representing the electrical resistance based on said electrical signal and to generate and output a control signal 148a, 148b dependent on the electrical resistance or the representing value. Furthermore, the feedback unit 130 and the control unit 150 are configured to receive the control signal 148a, 148b. In this context, the control signal is configured as a feedback control signal 148a and as a control unit control signal 148b, wherein the feedback control signal 148a is output to the feedback unit 130 and the control unit control signal 148b is output to the control unit 150. The only difference between these two control signals 148a, 148b only differ from each other in their different connections or different set-ups of the feedback unit 130 and the control unit 150, but not with regard to an information content concerning the electrical resistance or the value representing the electrical resistance.

The control unit 150 is configured to control the high-frequency voltage supply unit 120 in such a way as to be able to automatically switch between at least one first and one second operating mode, wherein the alternating voltage present at the electrodes 114, 118 is limited by the limit value $U_1$ in the first operating mode, and by the limit value $U_2$ in the second operating mode, wherein $U_1$ is greater than $U_2$. Furthermore, the control unit 150 controls the high-frequency voltage supply unit 120 in such a way that an automatic switching from the first operating mode into the second operating mode occurs if a rate of increase of the electrical resistance between the first and second electrodes 114, 118 exceeds a predetermined limit value G. In this context, the second limit value $U_2$ is chosen in such a way that it is between 50% and 80%, preferably 70%, of the first limit value $U_1$. The first limit value $U_1$ is between 80V and 200V, preferably 100V. In this exemplary embodiment, the control by the control unit 150 is executed via a corresponding voltage control signal 152 of the control unit 150 which is able to be received by the high-frequency voltage supply unit 120.

A user of the electrosurgical system 100 uses the alternating voltage to heat up the body tissue to be treated with it and, in doing so, hears due to the pitch of the output signal 134, how high the electrical resistance between the two electrodes 114, 118 is and, thus, also how much the respective body tissue has dried out. If the electrical resistance increases in the context of the treatment virtually abruptly, which corresponds to the typical development of the electrical resistance illustrated in FIG. 2, the heat output of the electrodes 114, 118 will be reduced by switching to a limit value $U_2$ for the alternating voltage. Thus, the rate of increase of the electrical resistance is reduced and the user has sufficient time for reacting to the output signal 134, for example by changing the position of the two electrodes 114, 118 at the body tissue.

Furthermore, the control unit 150 is configured to store the electrical resistance between the first electrode 114 and the second electrode 118 or a value representing the electrical resistance for a predetermined period of time. This enables the control unit 150 to determine the rate of increase of the electrical resistance by comparing the electrical resistance or the representing value at a current point in time with the electrical resistance or the representing value at an earlier point in time. In this case, the rate of increase is determined by estimating said rate of increase through the calculation of the difference.

In addition, the control unit 150 is configured to control the high-frequency voltage supply unit 120 in such a way that an automatic switching from the second operating mode into the first operating mode occurs if the electrical resistance between the first and second electrodes 114, 118 is below a predetermined limit value W. In this context, the predetermined limit value W is chosen in such a way that, in case that the two electrodes 114, 118 are in contact with tissue that is not dried out, an automatic switching into the first operating mode occurs. Thus, it can be ensured that the user of the electrosurgical system 100 does not have to deal with a manual switching of the heat output and thus is able to better focus on the positioning of the two electrodes 114, 118 at the body tissue to be treated. In the shown exemplary embodiment of the electrosurgical system 100, the applicator 110 is configured in such a way that it can be guided to the body tissue to be treated via a catheter.

In an exemplary embodiment that is not shown in the figures, the high-frequency voltage supply unit can be connected to a first and second electrode, without, however, being connected to the electrodes or the applicator. This means that the electrodes may be part of an external device which is not a component of the electrosurgical system pursuant to the invention.

In the non-illustrated exemplary embodiment of the electrosurgical system, the discernible output signal is configured as a visual signal which the user can, for example, observe by means of a monitor.

Figure 2:
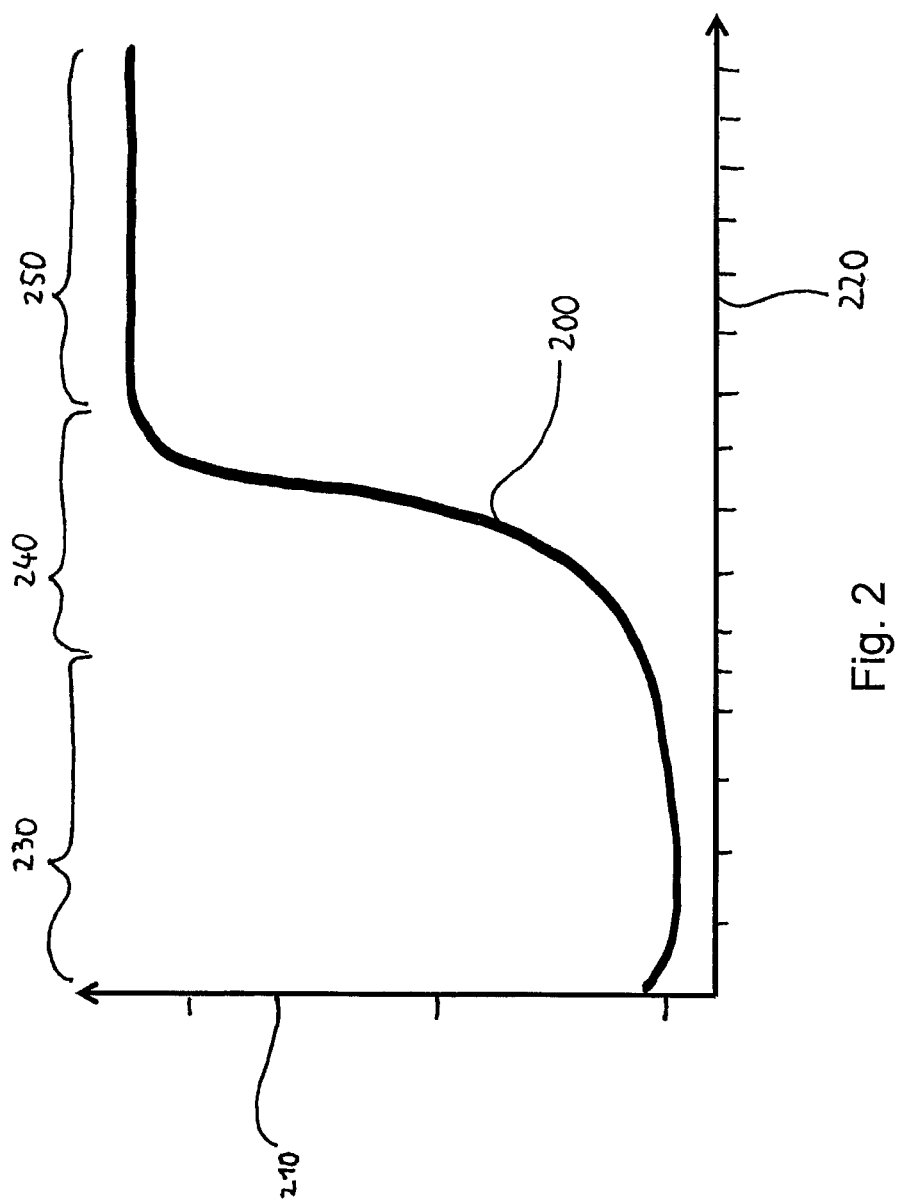
FIG. 2 a typical development of the electrical resistance between a first and second electrode over time during thermal necrosis of body tissue.

FIG. 2 shows a typical development 200 of the electrical resistance between a first and second electrode over time during thermal necrosis of body tissue;

The ordinate 210 shows the electrical resistance of the treated body tissue between the two electrodes in ohm, wherein a logarithmic presentation has been chosen which reaches from 10 ohm at the bottom line to 1000 ohm. On the abscissa 220 of the diagram illustrating the development 200, the time is marked in 2 second intervals.

As shown by the development 200, at the beginning of an ablation, a typical tissue resistance of body tissue is at approximately 10 ohm. In a heating phase 230 at the beginning of the ablation, the tissue is heated up, while the electrical resistance remains approximately the same. Subsequently, a jump phase 240 occurs, during which the tissue resistance increases virtually abruptly. During said jump phase 240, it is difficult for the user of the electrosurgical system to react quickly enough to the output signal, since the electrical resistance increases within only 2 to 5 seconds. After this jump of the electrical resistance, the tissue is in the dry out phase 250 and there is the risk that blood or tissue residue might stick to the two electrodes connected to the electrosurgical system and that the applicator might have to be cleaned.

In the context of an ablation proceeding as desired, the user would have to change the position of the electrodes during the jump phase 240 so quickly that the electrodes are moved in due time into the vicinity where the tissue is not dried out. Said tissue initially has once again a lower electrical resistance and is heated up by the electrode and a new heating phase 230 begins. As described in the context of FIG. 1, by reducing the heat output of the two electrodes during the jump phase 240, the control unit of the electrosurgical system pursuant to the invention is able to increase the duration of the jump phase 240 and to thus facilitate a reaction of the user to the abrupt increase of the electrical resistance of the tissue.

Figure 3:
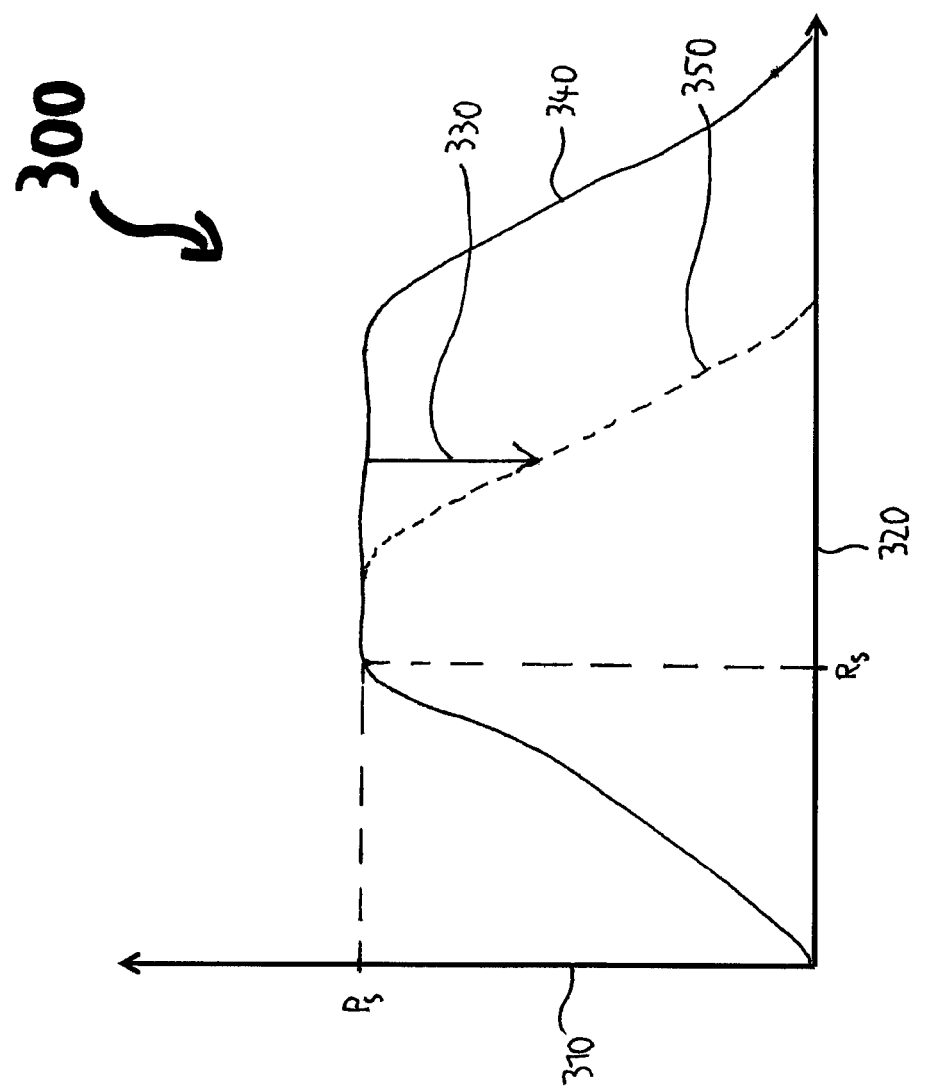
FIG. 3 a development of the dependency between a heat output during an ablation of body tissue and an electrical resistance, wherein an impact of a reduction of voltage from $U_1$ to $U_2$ is illustrated.

FIG. 3 shows a development of the dependency 300 between the heat output emitted into the tissue by a high-frequency voltage supply unit 120 during an ablation of body tissue and an electrical resistance, wherein an impact of a reduction 330 of the voltage limit value $U_1$ 340 to $U_2$ 350 is illustrated.

The ordinate 310 shows the heat output emitted via the two electrodes in watt. On the abscissa 320 of the diagram illustrating the dependency 300, the electrical resistance between the two electrodes is marked in ohm.

The dependency 300 shows that, in case of small resistances, the heat output increases along with the increasing electrical resistance of the body tissue. In this range, the heat output is limited by a maximum allowable output current. The heat output increases in this case proportionally to the resistance. Once the heat output has increased to a predetermined desired value, e.g. 18 watt, a limitation of the output occurs, in the context of which the output current and the output voltage are regulated in such a way that the heat output corresponds to the desired value. The output current decreases upon the increase of the resistance, while the output voltage increases upon the increase of the resistance. In the illustrated exemplary embodiment, the output limitation occurs at a heat output $P_s$ of 18 watt and a resistance $R_s$ of approximately 200 ohm. If the resistance increases further, the heat output is limited by the maximum allowable output voltage and decreases inversely proportionally to the resistance.

If the rate of increase of the electrical resistance increases to above a limit value G, which, in the illustrated exemplary embodiment, is the case at 550 ohm, the voltage reduction 330 occurs, through which the maximum allowable output voltage, i.e. the limit value of the output voltage is reduced from $U_1$ 340 with an amplitude of 100V to $U_2$ 350 with an amplitude of 70V. As illustrated by the diagram, this reduction 330 of the limit value can lead to a decrease of the heat output of approximately 50%.

If the control unit of the electrosurgical system switches from $U_1$ to the limit value $U_2$ with the smaller amplitude, the heat output emitted via the two electrodes is reduced so that, in accordance with the resistance development pursuant to FIG. 2, the user has more time to react to the increase of the tissue resistance between the first and second electrodes.

In this context, a voltage reduction due to a rate of increase of the resistance above the limit value G will typically occur in a resistance range of the tissue to be treated between 200 ohm and 700 ohm. In this case, the limit value G of the rate of increase is for example between 10 and 100 ohm/s, e.g. 50 ohm/s.

Figure 4:
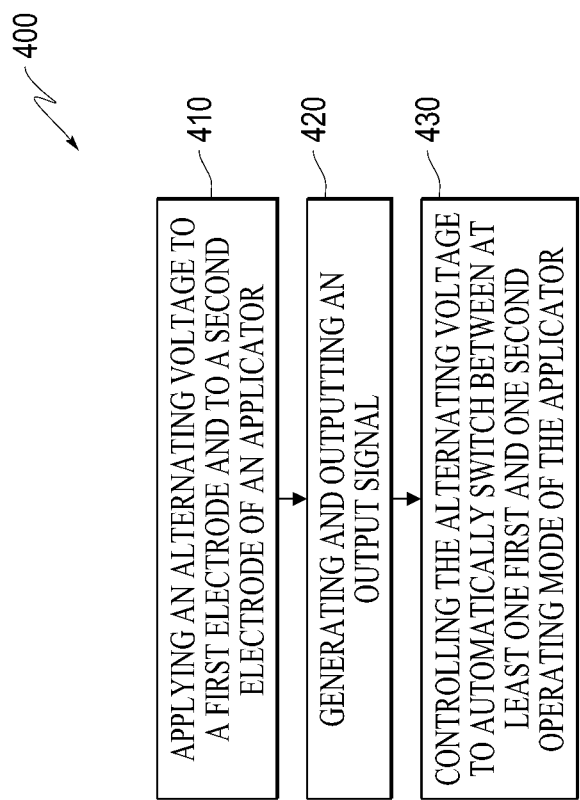
FIG. 4 a method pursuant to the invention for operating an electrosurgical system pursuant to another aspect of the invention.

FIG. 4 shows a method 400 pursuant to the invention for operating an electrosurgical system pursuant to another aspect of the invention. The method 400 comprises three method steps 410, 420, 430.

A first method step 410 consists in applying an alternating voltage to a first electrode and to a second electrode of an applicator.

In a second method step 420, an output signal is generated and output, wherein the output signal depends on an electrical resistance between the first and second electrodes.

The third method step 430 comprises controlling the alternating voltage in such a way as to be able to automatically switch between at least one first and one second operating mode of the applicator, wherein in the first operating mode the alternating voltage is limited by a first limit value $U_1$, and in the second operating mode the alternating voltage is limited by a second limit value $U_2$, wherein $U_1$ is greater than $U_2$, and wherein an automatic switching from the first operating mode into the second operating mode occurs if a rate of increase of the electrical resistance between the first and second electrodes exceeds a predetermined limit value G.

LIST OF REFERENCE NUMBERS 100 electrosurgical system
110 applicator
114 first electrode
118 second electrode
119 distal end
120 high-frequency voltage supply unit
130 feedback unit
134 output signal
138 loudspeaker
140 processing unit
145 electrical signal
148a feedback control signal
148b control unit control signal
150 control unit
152 voltage control signal
155 control knob
200 development of the electrical resistance
210 ordinate of FIG. 2
220 abscissa of FIG. 2
230 heating phase
240 jump phase
250 dry-out phase
300 dependency between heat output and resistance
310 ordinate of FIG. 3
320 abscissa of FIG. 3
330 voltage reduction
340 alternating voltage $U_1$
350 alternating voltage $U_2$
400 method pursuant to the invention
410 first method step
420 second method step
430 third method step

The invention claimed is:

1. An electrosurgical system for generating high-frequency alternating current for an ablation of body tissue, the electrosurgical system comprising:
a high-frequency voltage supply unit which is removably electrically connected to a first electrode and a second electrode, the high-frequency voltage supply unit being configured to supply the first and second electrodes with a high-frequency alternating voltage;
a feedback unit which is electrically connected to the first and second electrodes and which is configured to generate an output signal dependent on the electrical resistance between the first and second electrodes; and
a control unit configured to:
control the alternating voltage to automatically switch between at least one of: (i) a first operating mode in which the alternating voltage is limited by a predetermined maximum first voltage limit value $U_1$, and (ii) a second operating mode in which the alternating voltage is limited by a predetermined maximum second voltage limit value $U_2$, the predetermined second voltage limit value $U_2$ being nonzero, and
control the high-frequency voltage supply unit so that an automatic switching from the second operating mode back into the first operating mode occurs when the electrical resistance between the first and second electrodes is below a predetermined limit value W, wherein:
the first voltage limit value $U_1$ is greater than the second voltage limit value $U_2$, and
the first operating mode is automatically switched into the second operating mode in direct response to a rate of increase of the electrical resistance between the first and second electrodes exceeding a predetermined limit value G.

2. The electrosurgical system according to claim 1, further comprising:
a processing unit which is electrically connected to the first and second electrodes, the processing unit being configured to:
receive an electrical response signal, via the first and second electrodes, to determine the electrical resistance between the first and second electrodes or a value representing the electrical resistance based on the electrical response signal, and generate and output a control signal dependent on the electrical resistance or the representing value, wherein:

the feedback unit and the control unit are further configured to receive the control signal.

3. The electrosurgical system according to claim 1, wherein the second voltage limit value $U_2$ is between 50% and 80% of the first voltage limit value $U_1$.

4. The electrosurgical system according to claim 1, wherein the control unit is further configured to:

store the electrical resistance between the first and second electrodes or a value representing the resistance for a predetermined period of time, compare the electrical resistance or the representing value at a current point in time with the electrical resistance or the representing value at an earlier point in time, and determine the rate of increase of the electrical resistance.

5. The electrosurgical system according to claim 1, wherein:

the control unit is further configured to automatically switch between a number of further operating modes with further voltage limit values $U_3, \ldots, U_n$ of the alternating voltage with successively decreasing amplitudes which are smaller than an amplitude of the second voltage limit value $U_2$, and one of the operating modes $U_i$ is automatically switched into the operating mode with the next smaller amplitude when the rate of increase of the electrical resistance between the first and second electrodes exceeds a predetermined limit value assigned to the operating mode $U_i$.

6. The electrosurgical system according to claim 1, further comprising:

an applicator, where the first and the second electrodes form a bipolar electrode configuration in the applicator, wherein the first electrode is arranged at a rounded tip of a distal end of the applicator and the second electrode is arranged at a distance of between 0.5 cm and 3 cm from the first electrode at the distal end of the applicator.

7. The electrosurgical system according to claim 6, wherein the applicator is configured to be guided to the body tissue to be treated via a catheter.

8. A method of operating an electrosurgical system, the method comprising:

applying an alternating voltage to a first electrode and a second electrode of an applicator, generating and outputting an output signal dependent on an electrical resistance between the first and second electrodes, controlling the alternating voltage to automatically switch between at least one of: (i) a first operating mode in which the alternating voltage is limited by a predetermined maximum first voltage limit value $U_1$, and (ii) a second operating mode in which the alternating voltage is limited by a predetermined maximum second voltage limit value $U_2$, the predetermined second voltage limit value $U_2$ being nonzero, and controlling the alternating voltage to perform automatic switching from the second operating mode back into the first operating mode when the electrical resistance between the first electrode and the second electrode is below a predetermined limit value W, wherein:

the first voltage limit value $U_1$ is greater than the second voltage limit value $U_2$, and the first operating mode is automatically switched into the second operating mode in direct response to a rate of increase of the electrical resistance between the first and second electrodes exceeding a predetermined limit value G.

9. The method according to claim 8, further comprising:

determining the electrical resistance or a value representing the electrical resistance between the first and second electrodes, generating and outputting a control signal dependent on the electrical resistance, and storing the electrical resistance or the value representing the electrical resistance for a predetermined period of time, and determining the rate of increase of the electrical resistance by comparing the electrical resistance or the representing value at a current point in time with the electrical resistance or the representing value at an earlier point in time.

10. A method comprising:

applying the electrosurgical system according to claim 1 to a thermal necrosis of unwanted body tissue.

11. A method comprising:

applying and controlling an applicator during an ablation of unwanted tissue according to steps of the method according to claim 9.

\* \* \* \* \*